United States Patent
Menn et al.

(10) Patent No.: US 10,307,162 B2
(45) Date of Patent: *Jun. 4, 2019

(54) HERMETIC ROTATING HANDLE ASSEMBLY FOR A SURGICAL CLIP APPLIER FOR LAPAROSCOPIC PROCEDURES

(71) Applicant: CONMED Corporation, Utica, NY (US)

(72) Inventors: Pavel Menn, Marblehead, MA (US); Nathaniel Rosso, Gloucester, MA (US)

(73) Assignee: CONMED Corporation, Utica, NY (US)

( * ) Notice: Subject to any disclaimer, the term of this patent is extended or adjusted under 35 U.S.C. 154(b) by 317 days.

This patent is subject to a terminal disclaimer.

(21) Appl. No.: 15/238,435

(22) Filed: Aug. 16, 2016

(65) Prior Publication Data

US 2017/0100123 A1    Apr. 13, 2017

Related U.S. Application Data

(63) Continuation of application No. 14/224,499, filed on Mar. 25, 2014, now Pat. No. 9,468,444, which is a
(Continued)

(51) Int. Cl.
*A61B 17/10* (2006.01)
*A61B 17/128* (2006.01)
(Continued)

(52) U.S. Cl.
CPC ...... *A61B 17/105* (2013.01); *A61B 17/00234* (2013.01); *A61B 17/1285* (2013.01);
(Continued)

(58) Field of Classification Search
CPC .............. A61B 17/128; A61B 17/1285; A61B 17/2909; A61B 17/00234
See application file for complete search history.

(56) References Cited

U.S. PATENT DOCUMENTS

| | | | |
|---|---|---|---|
| 4,902,129 A | 2/1990 | Siegmund et al. | |
| 4,930,861 A | 6/1990 | Okabe et al. | |

(Continued)

FOREIGN PATENT DOCUMENTS

| | | |
|---|---|---|
| DE | 19603889 | 8/1997 |
| EP | 2090251 | 8/2009 |

(Continued)

OTHER PUBLICATIONS

Office Action for U.S. Appl. No. 13/081,480, dated Aug. 29, 2013, 5 pages.

(Continued)

*Primary Examiner* — Kathleen S Holwerda
*Assistant Examiner* — Christina C Lauer
(74) *Attorney, Agent, or Firm* — Fredrick J M Price; Bond, Schoeneck & King, PLLC

(57) ABSTRACT

This invention provides hermetically-sealed handle assembly with a rotating trigger for use with disposable components, such as surgical clip appliers. The rotating trigger reduces the gripping force necessary to fully control the internal actuator mechanism to operate a disposable surgical clip applier to fully ligate a vessel or other tissue. The hermetic seal on the handle assembly prevents any patient fluids and other bioburden from entering the internal structures. This reduces the possibility of cross-contamination and the costs of sterilization.

17 Claims, 5 Drawing Sheets

Related U.S. Application Data continuation of application No. 13/081,480, filed on Apr. 6, 2011, now Pat. No. 8,715,299.

(60) Provisional application No. 61/321,237, filed on Apr. 6, 2010.

(51) Int. Cl.
*A61B 17/29* (2006.01)
*A61B 90/00* (2016.01)
*A61B 17/00* (2006.01)

(52) U.S. Cl.
CPC .......... *A61B 17/2909* (2013.01); *A61B 90/08* (2016.02); *A61B 2017/0046* (2013.01); *A61B 2017/00477* (2013.01); *A61B 2017/2925* (2013.01); *A61B 2090/0813* (2016.02)

(56) References Cited

U.S. PATENT DOCUMENTS

| | | | |
|---|---|---|---|
| 5,056,902 A | 10/1991 | Chinnock et al. | |
| 5,363,839 A | 11/1994 | Lankford | |
| 5,431,667 A * | 7/1995 | Thompson | A61B 17/122 606/139 |
| 5,447,513 A * | 9/1995 | Davison | A61B 17/1285 227/901 |
| 5,484,095 A | 1/1996 | Green et al. | |
| 5,499,992 A | 3/1996 | Meade et al. | |
| 5,618,291 A | 4/1997 | Thompson et al. | |
| 5,772,673 A | 6/1998 | Cuny et al. | |
| 5,836,867 A | 11/1998 | Speier et al. | |
| 5,899,851 A | 5/1999 | Koninckx | |
| 5,978,161 A | 11/1999 | Lemke | |
| 6,059,799 A | 5/2000 | Aranyi et al. | |
| 6,097,423 A | 8/2000 | Mattsson-Boze et al. | |
| 6,099,537 A | 8/2000 | Sugai et al. | |
| 6,425,857 B1 | 7/2002 | Rudischhauser et al. | |
| 6,682,528 B2 | 1/2004 | Frazier et al. | |
| 6,955,644 B2 | 10/2005 | Forkey et al. | |
| 7,717,926 B2 | 5/2010 | Whitfield et al. | |
| 7,857,183 B2 | 12/2010 | Shelton, IV | |
| 8,075,573 B2 | 12/2011 | Gambale et al. | |
| 8,397,971 B2 | 3/2013 | Yates et al. | |
| 8,414,577 B2 | 4/2013 | Boudreaux et al. | |
| 8,715,299 B2 | 5/2014 | Menn et al. | |
| 2003/0040745 A1 | 2/2003 | Frazier et al. | |
| 2004/0167545 A1 | 8/2004 | Sadler et al. | |
| 2006/0025811 A1 | 2/2006 | Shelton | |
| 2006/0079912 A1 | 4/2006 | Whitefield | |
| 2007/0074762 A1 | 4/2007 | Menn | |
| 2009/0228024 A1 | 10/2009 | Whitfield et al. | |
| 2013/0245615 A1 | 9/2013 | Koltz | |
| 2014/0296879 A1 | 10/2014 | Menn et al. | |

FOREIGN PATENT DOCUMENTS

| | | |
|---|---|---|
| WO | WO2011/127223 | 10/2011 |
| WO | WO2015/106099 | 7/2015 |

OTHER PUBLICATIONS

Office Action for U.S. Appl. No. 14/224,499, dated Aug. 14, 2015, 8 pages.
International Search Report and Written Opinion for International Application No. PCT/US2011/031484, dated May 27, 2011.
International Preliminary Report on Patentability for International Application No. PCT/US2011/031484, dated Oct. 9, 2012.
International Search Report and Written Opinion for International Application No. PCT/US2015/010814, dated Apr. 28, 2015.
International Preliminary Report on Patentability for International Application No. PCT/US2015/010814, dated Jul. 12, 2016.

* cited by examiner

HERMETIC ROTATING HANDLE ASSEMBLY FOR A SURGICAL CLIP APPLIER FOR LAPAROSCOPIC PROCEDURES

CROSS REFERENCE TO RELATED APPLICATION

This application claims the benefit of U.S. Provisional Patent Application No. 61/321,237 filed on Apr. 6, 2010, the contents of which are incorporated herein by reference.

FIELD OF THE INVENTION

This invention relates to a novel hermetic rotating handle assembly for a surgical clip applier for laparoscopic or endoscopic procedures.

BACKGROUND OF INVENTION

Laparoscopic and endoscopic surgical procedures are conducted through a small incision in the skin or natural body orifices. In order to operate, surgeons must use instruments that have a small enough cross section to fit within these small openings and long enough to reach the surgical area within the body.

Surgical instruments designed for these procedures are often separated into two components to reduce costs and minimize cross contamination.

The first component is a long and narrow disposable portion that is inserted into the small opening during surgery. These disposable components contain surgical tools, such as surgical jaws or surgical clip appliers, dissectors or other instruments, on the end which enters the patient. These disposable components also contain small actuators which control the operation of the surgical tools within the patient.

These small actuators on the first component are operatively attached to the second component of these surgical instruments. The second component is a non-disposable control unit for moving the long disposable component within the patient and operating the actuators to control the surgical tools on the disposable component. The second component is often a handle with a trigger. A surgeon may control the movement and placement of the disposable component by holding the handle and operate the small actuators by squeezing the trigger. For instance, a surgeon may squeeze the trigger to place a surgical clip over a vessel.

By separating these two components, the risk of cross contamination between separate patients or separate tissues on the same patient is reduced. The non-disposable control unit does not enter the patient and the contaminated long and narrow component is simply disposed after each surgical procedure is completed. In addition, costs are saved since medical providers only need to replace the disposable component between surgical procedures.

However, one the problems with currently existing surgical instruments used in these procedures is the possible contamination of the non-disposable control unit. This non-disposable component may still contact patient fluids during surgeries and become contaminated. This may be especially problematic for handle and trigger assemblies. In order for a trigger to be squeezed and moveable, these assemblies have openings to their internal structures.

One solution to this problem is for medical providers to autoclave and sterilize each non-disposable component after each surgical procedure. However, the time needed to autoclave and sterilize these non-disposable handle and trigger assemblies is significantly high due to the need to sterilize the internal structures. This sterilization increases maintenance costs for medical providers. Current surgical clip appliers include many disposable handles since they cannot be sterilized effectively, even with hours in an autoclave.

Accordingly, the subject invention is a non-disposable hermetically-sealed handle assembly with a rotating trigger for use with disposable components, such as surgical clip appliers. The hermetic seal on the handle assembly prevents any patient fluids and other bioburden from entering the internal structures. This reduces the possibility of cross-contamination and the costs of sterilization.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses an endoscopic surgical tool comprising, a housing comprising an upper portion and a handle; an actuating mechanism contained within the housing along a first axis, wherein the actuating mechanism is adapted to operatively couple to a disposable external shaft that extends away from the housing along a first shaft axis from a proximal end to a distal end, wherein the first axis and the first shaft axis are substantially parallel; a lever coupled at a proximal end to the actuating mechanism and extending in a downward direction, wherein the lever is pivotably coupled at a distal end to an internal shaft that extends along a second shaft axis that is substantially perpendicular to the first shaft axis; a first end of the internal shaft extending through a first opening in the housing proximate to the top of the handle, and further extending through a central opening of a first disc spring; a second end of the internal shaft extending through a second opening in the housing proximate to the top of the handle, and further extending through a central opening of a second disc spring, wherein the first opening and the second opening are substantially parallel with each other; a first trigger shaft comprising a first substantially semi-spherical top portion coupled to the first end of the internal shaft after extending through the first disc spring, wherein the first trigger shaft further comprises a first substantially half-cylindrical lower portion with a first substantially flat surface, wherein the first disc spring provides a first seal about the first end of the internal shaft by providing a first compressive force on the first substantially semi-spherical top portion of the first trigger shaft and an opposing second compressive force on the exterior surface about the first opening in the housing; a second trigger shaft comprising a second substantially semi-spherical top portion coupled to the second end of the internal shaft after extending through the second disc spring, wherein the second trigger shaft further comprises a second substantially half-cylindrical lower portion with a second substantially flat surface, wherein the second disc spring provides a second seal about the second end of the internal shaft by providing a third compressive force on the second substantially semi-spherical top portion of the second trigger shaft and an opposing fourth compressive force on the exterior surface about the second opening in the housing, wherein the first and second substantially flat surface of the first and second trigger shafts couple to form a substantially cylindrical lower trigger shaft defining a longitudinal axis; a hollow substantially cylindrical trigger grip coupled over the cylindrical lower trigger shaft; wherein application of compressive force to the trigger grip towards the handle rotates the cylindrical lower trigger shaft about the longitudinal axis in a first direction to rotate the first and second ends of the internal shaft in a direction away from the second shaft axis, wherein rotation of the internal shaft pivots the coupled lever to operate the actuating mechanism.

In another embodiment of the subject invention, the first and second trigger shafts comprise complementary configurations.

In another embodiment of the subject invention, the external shaft comprises a cartridge containing surgical clips.

In another embodiment of the subject invention, the distal end of the external shaft is adapted to receive an end effector.

In another embodiment of the subject invention, the end effector comprises a distally attached surgical jaws assembly.

In another embodiment of the subject invention, the first and second disc springs comprise conical spring washers.

In another embodiment of the subject invention, the housing is non-disposable.

In another embodiment of the subject invention, the cylindrical lower trigger shaft rotates about the longitudinal axis in a second direction, opposite the first direction, when the trigger is released.

In another embodiment of the subject invention, the housing comprises a single piece.

In another embodiment of the subject invention, the housing comprises two coupled pieces with complementary configurations.

The subject invention also discloses a hermetically sealed handle assembly for a surgical clip applier comprising: a housing comprising an upper portion and a lower handle; an actuating mechanism contained within the upper portion of the housing that controls a disposable cartridge containing surgical clips; a shaft extending from the housing containing rotating means so as to permit rotation of the shaft about an axis that extends substantially longitudinally through the shaft, wherein the shaft rotates in a first direction about an axis that extends substantially longitudinally through the shaft when a gripping force is applied to the shaft, and further wherein the actuating mechanism within the housing is coupled to the shaft such that rotation of the shaft operates the actuating mechanism.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

Figure 1:
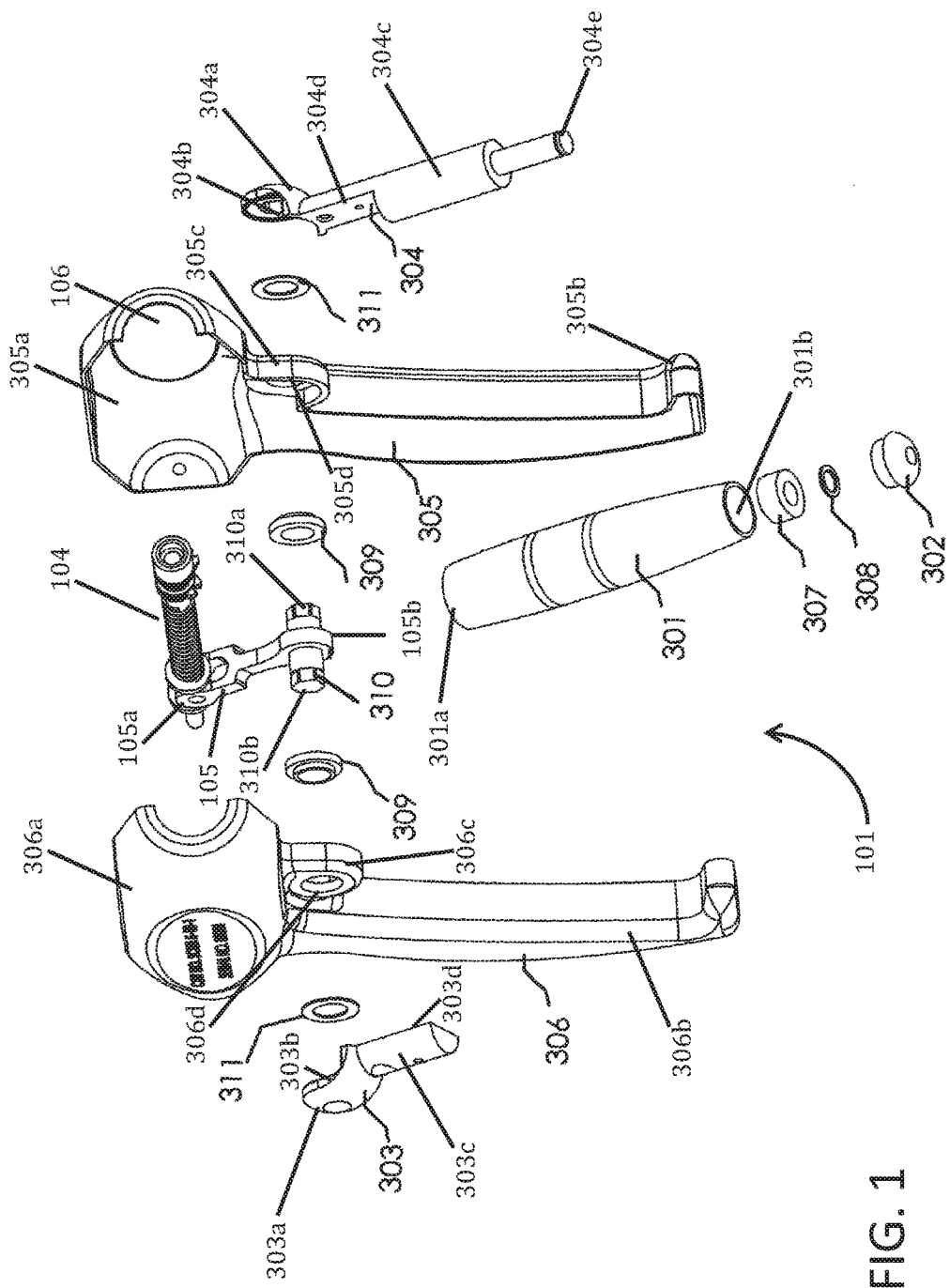
FIG. 1 illustrates an exploded view of a hermetically-sealed rotating trigger and handle assembly for a clip applier.
Figure 2:
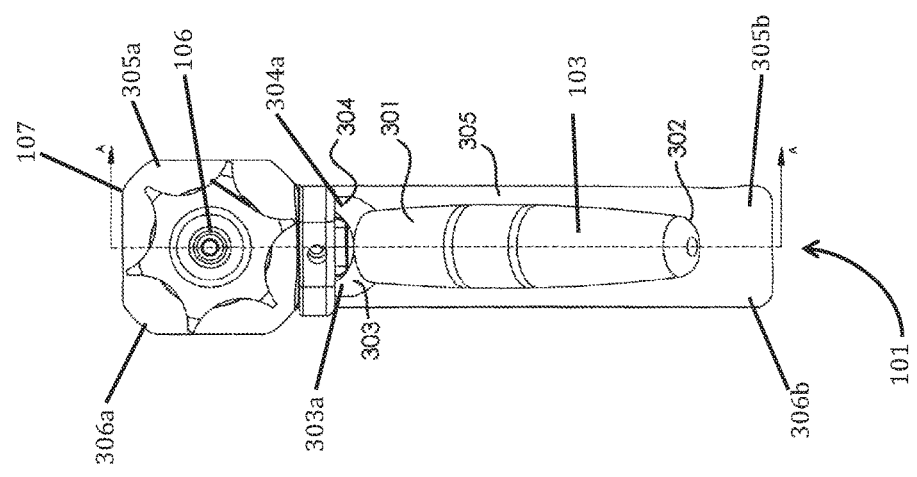
FIG. 2 illustrates a front view of the hermetically-sealed rotating trigger and handle assembly.
Figure 3:
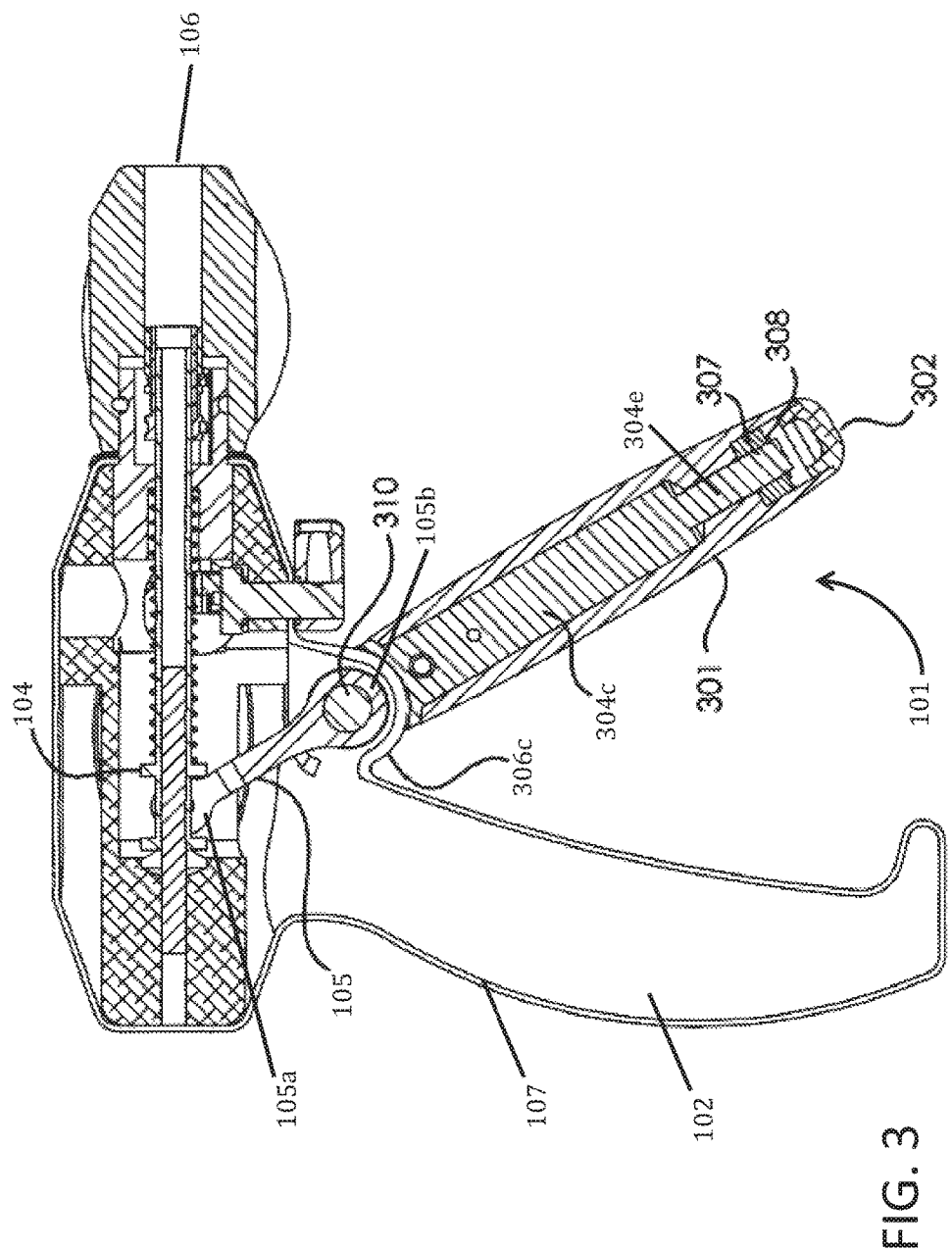
FIG. 3 illustrates a side cross-sectional view of the hermetically-sealed rotating trigger and handle assembly along line "A" of FIG. 2.
Figure 4:
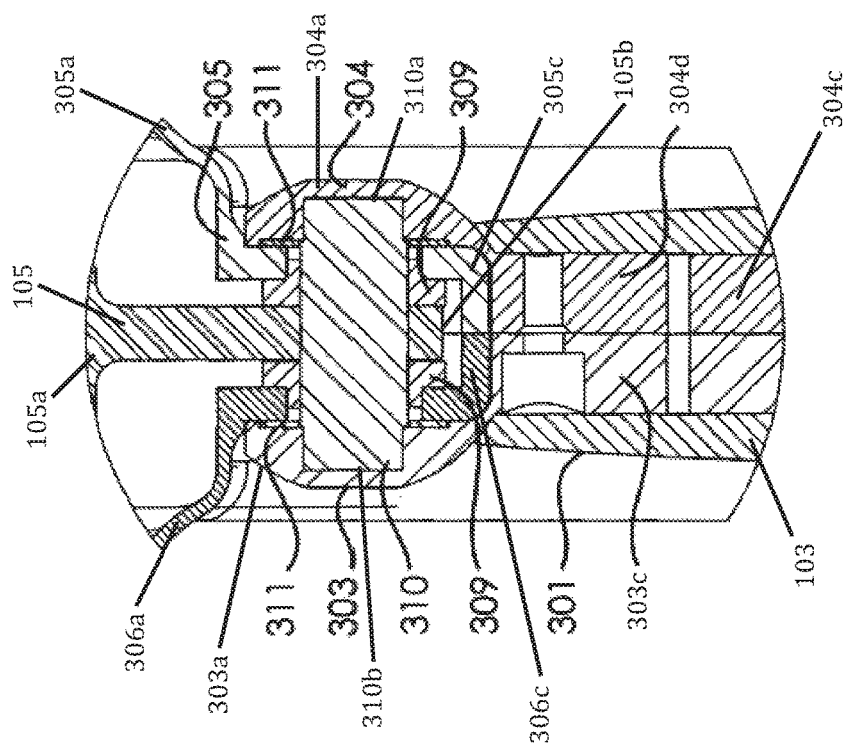
FIG. 4 illustrates a cross-sectional front internal view of the hermetically-sealed rotating trigger and handle assembly.

FIGS. 1-5 illustrate a hermetically-sealed handle and trigger assembly 101 with a handle 102 and a rotating trigger 103 for a surgical clip applier (not shown). FIG. 3 illustrates a side cross-sectional view of the handle and trigger assembly 101 as shown by lines "A" of FIG. 2. The hermetic seal on the handle and trigger assembly 101 prevents any patient fluids from entering the internal structures. This reduces the possibility of cross-contamination and the costs of sterilization, which allows the handle and trigger assembly 101 to be non-disposable.

The rotating trigger 103 rotates in a first direction that is substantially perpendicular to the length of the trigger 103 when squeezed in a direction towards handle 102. The rotating trigger 103 rotates in a second direction, opposite the first direction, when released and moving away from handle 102.

The elements of the handle and trigger assembly 101 include an external housing 107 that is formed by a hollow left half section 305 and a hollow right half section 306. Hollow left half section 305 and hollow right half section 306 are complementarily shaped to each other. The housing 107 may be made of a polycarbonate, ABS, stainless steel or other suitable material known to those skilled in the art. The separate half sections 305 and 306 may be attached together by adhesives, fasteners, welding, or other attachment means known to those skilled in the art.

Left half section 305 has an upper left housing 305a, a lower left half-handle housing 305b and a hollow left hinge housing 305c. Hollow left hinge housing 305c has a traversing left opening 305d.

Right half section 306 has an upper right housing 306a, a lower right half-handle housing 306b, and a hollow right hinge housing 306c. Hollow right hinge housing 306c has a traversing right opening 306d.

An actuator mechanism 104 is contained within upper left housing 305a and upper right housing 306a. Once the left half section 305 and the right half section are connected to form the external housing 107, the upper left housing 305a and the upper right housing 306a form housing opening 106. This opening 106 contains the actuator mechanism 104 and allows it to control the disposable cartridge containing surgical clips and a plurality of distal end effectors. The internal actuator mechanism 104 of the subject invention may be any mechanism, known to those skilled in the art, which operates a cartridge containing surgical clips and a distal end effector that is controllable with pivotable lever 105.

A pivotable lever 105 has a top end 105a and a bottom end 105b. The top end 105a of lever 105 is operatively connected to actuator mechanism 104. Trigger shaft 310 is substantially perpendicular to lever 105. The top end 105a of lever 105 may pivot about the pivot point of bottom end 105b by rotating around the axis of trigger shaft 310.

Trigger shaft 310 has a left end 310a and a right end 310b. Trigger shaft bearings 309 are placed over left end 310a and right end 310b.

Left end 310a passes through left opening 305d of left hinge housing 305 and then passes through a spring seal washer 311. A left hinge element of the trigger 304 has an upper semi-spherical portion 304a with an indentation 304b that houses the spring seal washer 311. After passing through spring seal washer 311, left end 310a of trigger shaft 310 attaches within indentation 304b of the left hinge element of the trigger 304.

Right end 310b passes through left opening 306d of right hinge housing 306 and then passes through a spring seal washer 311. A right hinge element of the trigger 303 has an upper semi-spherical portion 303a with an indentation 303b. After passing through spring seal washer 311, right end 310b of trigger shaft 310 attaches within indentation 303b of the right hinge element of the trigger 303.

Right hinge element of the trigger 303 has a lower trigger spine 303c attached to upper semi-spherical portion 303a. Lower trigger spine 303c has a half-cylindrical shape with a substantially flat face 303d.

Left hinge element of the trigger 304 has a middle trigger spine 304c attached to upper semi-spherical portion 304a. The upper section of middle trigger spine 304c, proximate to semi-spherical portion 304a, has a half-cylindrical shape with a substantially flat face 304d. The lower section of middle trigger spine 304c, distal to semi-spherical portion 304a, has a substantially cylindrical shape. Left hinge element of the trigger 304 also has a lower substantially cylindrical trigger spine 304e attached to middle trigger spine 304c.

As left end 310a attaches within indentation 304b and right end 310b attaches within indentation 303b, substantially flat face 303d is attached to the opposing substantially flat face 304d above the lower section of middle trigger spine 304c. Once joined, flat faces 303d and 304d form a substantially cylindrical shape that is substantially equivalent in diameter to the lower section of middle trigger spine 304c. The right hinge element of the trigger 303 is torsionally fixed to the right end 310b of trigger shaft 310. The left hinge element of the trigger 304 is torsionally fixed to the left end 310a of trigger shaft 310.

A hollow substantially cylindrical trigger grip 301 has a top opening 301a and a bottom opening 301b. The trigger grip 301 is placed over the connected right hinge element 303 and left hinge element 304 through top opening 301a. The lower trigger spine 304e of left hinge element of the trigger 304 passes through bottom opening 301b, a bushing 307, a retaining ring 308 and is attached to an end cap 302.

Figure 5:
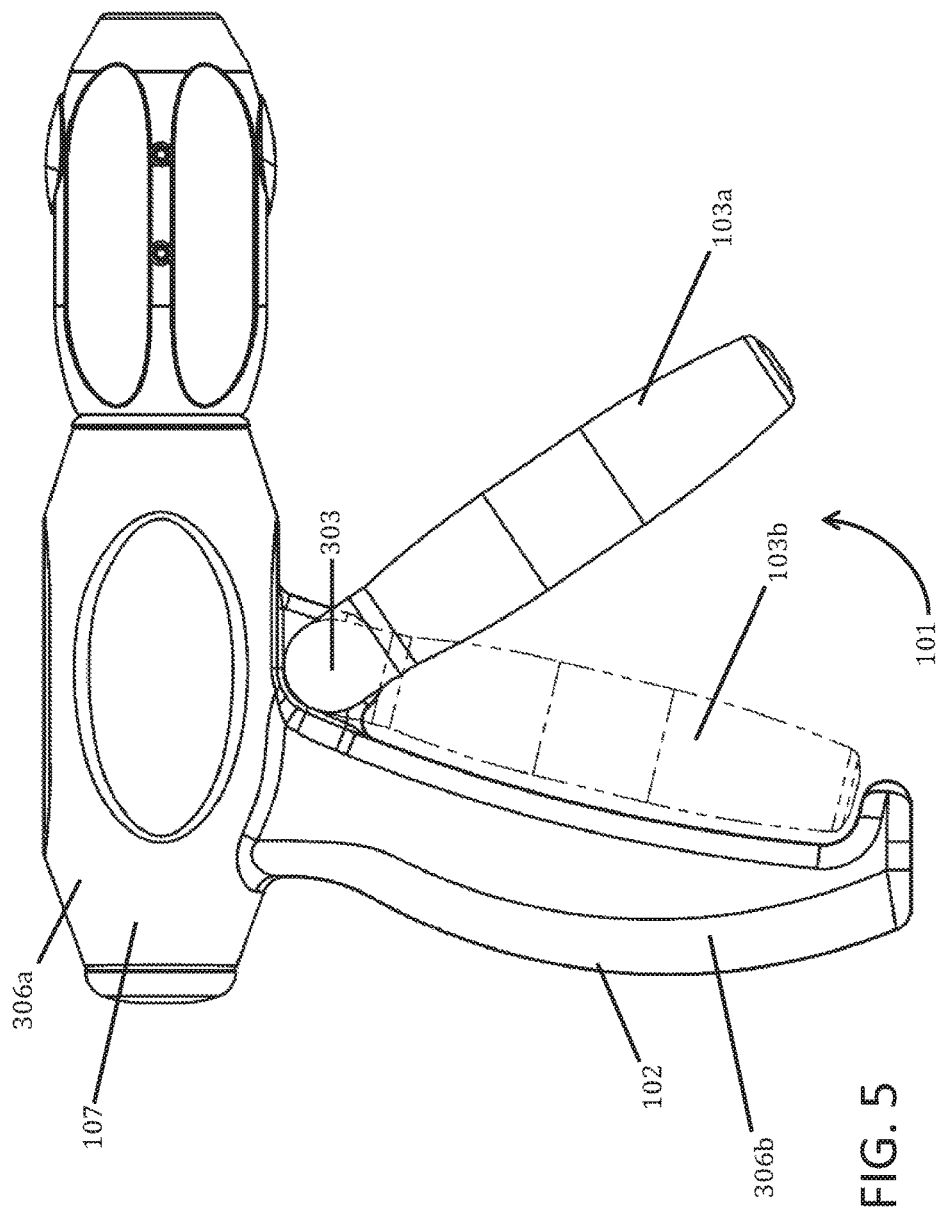
FIG. 5 illustrates a side view of the hermetically-sealed rotating trigger and handle assembly.

FIG. 5 illustrates the rotating trigger in the resting position 103a and the squeezed position 103b. When a user applies gripping force to the trigger grip 301 by squeezing rotating trigger 103, the trigger grip 301, the lower trigger spine 303c, and the middle trigger spine 304c all begin to rotate about the axis of trigger shaft 310 in either a clockwise or counterclockwise direction. As trigger spine 304c begins to rotate, the left end 310a of trigger shaft 310 also begins to rotate in the same direction. Concurrently, as trigger spine 303c begins to rotate, the right end 310b of trigger shaft 310 also begins to rotate in the same direction. The rotation of trigger shaft 310 causes the top end 105a of lever 105 to begin to pivot about the about the pivot point of bottom end 105b by rotating around trigger shaft 310. The pivoting of top end 105a operates actuator mechanism 104 which controls the surgical clip applier distal end effector (not shown). Thus, application of gripping force to the trigger 103 operates the surgical clip applier.

Once a user releases the trigger grip 301, the trigger grip 301, the lower trigger spine 303c, and the middle trigger spine 304c all begin to rotate about the axis of trigger shaft 310 in the opposite clockwise or counterclockwise direction The trigger shaft 310 rotating in an opposite direction causes the top end 105a of lever 105 to begin to pivot in an opposite direction about the about the pivot point of bottom end 105b by rotating around trigger shaft 310. The opposite pivoting of top end 105a releases the actuator mechanism 104 which controls the surgical clip applier distal end effector (not shown). Thus, release of gripping force to the trigger 103 stops the operation of the surgical clip applier.

The rotating trigger 103 reduces the gripping force necessary to fully pivot lever 105 to operate actuator mechanism 104 to operate a disposable surgical clip applier (not shown) to fully ligate a vessel or other tissue. In one embodiment of the subject application the gripping force required to fully actuate for full ligation is reduced from 25 lbs to 5 lbs.

The trigger assembly 101 and the rotating trigger 103 remain hermetically sealed in the resting 103a and squeezed 103b positions. A spring seal washer 311 around the left end 310a of trigger shaft 310 provides a compressive force against semi-spherical portion 304a and an opposing compressive force against housings 305a and 305c. Another spring seal washer 311 around the right end 310b of trigger shaft 310 provides a compressive force against semi-spherical portion 303a and an opposing compressive force against housings 306a and 306c. These opposing compressive forces on both sides and surrounding trigger shaft 310 provide an air seal between trigger 103 and housing 107. This air seal is maintained during rotation of trigger 103 from the resting 103a to squeezed position 103b.

Handle and trigger assembly 101 does not require a change of the trigger body volume inside the handle when the trigger 103 is gripped or released. This allows the handle and trigger assembly 101 to contain a completely air tight seal, making the assembly 101 infinitely reusable while reducing sterilization time. This also minimizes autoclave ineffectiveness and the possibility of cross contamination from patient to patient.

In embodiments of the subject invention, the washer seals 311, the bushing 307, the retaining ring 308 and the trigger shaft bearings 309 may be composed of titanium, plastic, steel or any combination thereof. In another embodiment of the subject invention, the washer seals 311, the bushing 307, the retaining ring 308 and the trigger shaft bearings 309 may all be composed of a unitary construction.

What is claimed is:
1. A endoscopic surgical tool, comprising:
a housing comprising a hermetically-sealed handle assembly;

a trigger shaft having a first portion, a second portion, and defining a first axis, the first portion extending through a first opening in the housing, and the second portion extending through a second opening in the housing;

a first sealing member disposed and configured to hermetically seal the first portion of the trigger shaft extending through the first opening in the housing;

a second sealing member disposed and configured to hermetically seal the second portion of the trigger shaft extending through the second opening in the housing; and a trigger grip operably coupled to the first portion of the trigger shaft and to a trigger spine and operably coupled to the second portion of the trigger shaft, the trigger grip configured to rotate about a second axis in a clockwise direction or a counterclockwise direction when actuating the endoscopic surgical tool and applying a force to the trigger grip in a direction toward the handle assembly.

2. The endoscopic surgical tool of claim 1, wherein the first axis and the second axis are substantially perpendicular.

3. The endoscopic surgical tool of claim 1, wherein the first sealing member and the second sealing member comprise spring seal washers.

4. The endoscopic surgical tool of claim 1, wherein the first sealing member and the second sealing member comprise disc springs.

5. The endoscopic surgical tool of claim 1, wherein the housing is nondisposable.

6. The endoscopic surgical tool of claim 1, wherein the housing comprises a single piece.

7. The endoscopic surgical tool of claim 1, wherein the housing comprises two coupled pieces with complementary configurations.

8. An apparatus, comprising:

a housing comprising a handle assembly;

a trigger shaft, the trigger shaft having a first portion, a second portion, and defining a first axis, the first portion extending through a first opening in the housing, and the second portion extending through a second opening in the housing; and a trigger assembly including a rotating trigger, the rotating trigger operably coupled to the first portion of the trigger shaft and operably coupled to the second portion of the trigger shaft, the rotating trigger configured to rotate about the first axis, wherein the rotating trigger comprises:

a trigger spine operably coupled to the first portion of the trigger shaft and operably coupled to the second portion of the trigger shaft, the trigger spine defining a second axis; and a trigger grip coupled to the trigger spine, the trigger grip disposed and configured to rotate about the second axis defined by the trigger spine, wherein the trigger grip is configured to rotate about the second axis in a clockwise direction or a counterclockwise direction when a force is applied to the trigger grip in a direction towards the handle assembly.

9. The apparatus of claim 8, further comprising:

a first trigger shaft bearing disposed around the first portion of the trigger shaft and coupled to the housing; and a second trigger shaft bearing disposed around the second portion of the trigger shaft and coupled to the housing.

10. The apparatus of claim 8, further comprising:

a first sealing member disposed around the first portion of the trigger shaft; and a second sealing member disposed around the second portion of the trigger shaft.

11. The apparatus of claim 10, wherein the first sealing member and the second sealing member are configured to prevent bioburden from entering an inner volume.

12. An apparatus, comprising:

a housing comprising a hermetically-sealed handle assembly;

a trigger shaft having a first portion, a second portion, and defining a first axis, the first portion extending through a first opening in the housing, and the second portion extending through a second opening in the housing;

a first sealing member disposed and configured to hermetically seal the first portion of the trigger shaft extending through the first opening in the housing;

a second sealing member disposed and configured to hermetically seal the second portion of the trigger shaft extending through the second opening in the housing; and a trigger assembly operably coupled to the first portion of the trigger shaft and operably coupled to the second portion of the trigger shaft, wherein the trigger assembly includes a rotating trigger, the rotating trigger operably coupled to the first portion of the trigger shaft and operably coupled to the second portion of the trigger shaft, the rotating trigger configured to rotate about the first axis, wherein the rotating trigger comprises:

a trigger spine operably coupled to the first portion of the trigger shaft and operably coupled to the second portion of the trigger shaft, the trigger spine defining a second axis, and a trigger grip coupled to the trigger spine, the trigger grip disposed and configured to rotate about the second axis defined by the trigger spine, wherein the trigger grip is configured to rotate about the second axis in a clockwise direction or a counterclockwise direction when a force is applied to the trigger grip in a direction towards the handle assembly.

13. The apparatus of claim 12, wherein the first sealing member and the second sealing member provide a force between the housing and the trigger assembly.

14. The apparatus of claim 13, wherein the first sealing member and the second sealing member comprise disc springs.

15. The apparatus of claim 13, wherein the first sealing member and the second sealing member comprise spring seal washers.

16. The apparatus of claim 12, wherein the first sealing member and the second sealing member provide an air seal between the housing and the trigger assembly.

17. The apparatus of claim 12, wherein the first sealing member and the second sealing member are configured to prevent bioburden from entering an inner volume of the housing.

* * * * *